United States Patent
Duran et al.

(10) Patent No.: US 11,465,755 B1
(45) Date of Patent: Oct. 11, 2022

(54) AIRCRAFT AIR QUALITY TESTING SYSTEM

(71) Applicant: Government of the United States, as represented by the Secretary of the Air Force, Wright-Patterson AFB, OH (US)

(72) Inventors: Christin M. Duran, Dayton, OH (US); Daniel O. Reilly, Kettering, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 826 days.

(21) Appl. No.: 16/379,848

(22) Filed: Apr. 10, 2019

Related U.S. Application Data

(60) Provisional application No. 62/664,405, filed on Apr. 30, 2018.

(51) Int. Cl.
*B64D 13/06* (2006.01)
*G01N 33/00* (2006.01)

(52) U.S. Cl.
CPC ......... *B64D 13/06* (2013.01); *G01N 33/0036* (2013.01); *G01N 33/0073* (2013.01); *B64D 2013/0651* (2013.01); *B64D 2013/0677* (2013.01); *G01N 2033/0068* (2013.01)

(58) Field of Classification Search
CPC ............ B64D 13/06; B64D 2013/0651; B64D 2013/0677; G01N 33/0036; G01N 33/0073; G01N 2033/0068
See application file for complete search history.

(56) References Cited

U.S. PATENT DOCUMENTS

| 4,109,509 | A | | 8/1978 | Cramer et al. | |
|---|---|---|---|---|---|
| 4,569,235 | A | * | 2/1986 | Conkle | G01N 33/0016 73/863.03 |
| 4,651,728 | A | * | 3/1987 | Gupta | A62B 7/14 128/201.28 |
| 4,786,472 | A | * | 11/1988 | McConnell | G01N 1/24 73/23.31 |

(Continued)

FOREIGN PATENT DOCUMENTS

| DE | 102006016541 B4 * | 5/2014 | ............. B64D 13/06 |
|---|---|---|---|
| WO | WO-02063294 A2 * | 8/2002 | ............... G01N 1/26 |

*Primary Examiner* — Emmanuel E Duke
(74) *Attorney, Agent, or Firm* — AFMCLO/JAZ; Timothy M. Barlow

(57) ABSTRACT

An aircraft air quality testing system includes a portable housing unit to be removably placed within an aircraft; an air testing unit secured inside the portable housing unit and including: a sensor to receive an air sample during a plurality of oxygen generation system cycles and engine thrust settings of the aircraft; a removable collection media to receive the air sample from the sensor and filter targeted chemicals from the air sample; and a plurality of analyzers to perform a real-time chemical analysis of the air sample and the filtered targeted chemicals. A first computer is operatively connected to the portable housing unit and includes: a processor to receive the real-time chemical analysis and generate real-time chemical analysis and flow rate data; a memory device to store the real-time chemical analysis and flow rate data; and a display device operatively connected to the portable housing unit.

20 Claims, 15 Drawing Sheets

(56) References Cited

U.S. PATENT DOCUMENTS

| | | | |
|---|---|---|---|
| 4,799,476 A | | 1/1989 | McGrady |
| H1039 H | | 4/1992 | Tripp, Jr. et al. |
| 5,372,134 A | | 12/1994 | Richardson |
| 5,791,982 A | | 8/1998 | Curry et al. |
| 6,452,510 B1 | | 9/2002 | Zysko |
| 6,744,373 B2 | | 6/2004 | Koyano et al. |
| 7,246,620 B2 | | 7/2007 | Conroy, Jr. |
| 7,251,550 B2 | * | 7/2007 | Eschborn ............ G05B 23/0254 701/33.9 |
| 7,302,313 B2 | * | 11/2007 | Sharp ....................... G01N 1/26 700/282 |
| 8,899,097 B2 | | 12/2014 | Wu |
| 9,089,721 B1 | * | 7/2015 | Horstman ................ A62B 7/14 |
| 9,102,417 B1 | * | 8/2015 | Young .................. A61B 5/6814 |
| 9,493,243 B2 | | 11/2016 | Lewis et al. |
| 9,651,501 B2 | | 5/2017 | Muller et al. |
| 9,873,523 B2 | | 1/2018 | Bothier |
| 9,957,052 B2 | * | 5/2018 | Fox ........................ B64D 13/06 |
| 10,011,370 B2 | | 7/2018 | Saptharishi et al. |
| 2013/0312744 A1 | * | 11/2013 | Kshirsagar ............. B64D 13/02 128/204.23 |
| 2015/0308383 A1 | * | 10/2015 | Hoffjann ................ B64D 27/24 60/269 |
| 2016/0306725 A1 | | 10/2016 | Hare et al. |
| 2016/0361678 A1 | * | 12/2016 | Blackley .................. A24F 40/48 |
| 2018/0148180 A1 | | 5/2018 | Fagundes et al. |
| 2018/0148182 A1 | | 5/2018 | Fagundes et al. |
| 2018/0188166 A1 | | 7/2018 | Zeller et al. |

\* cited by examiner

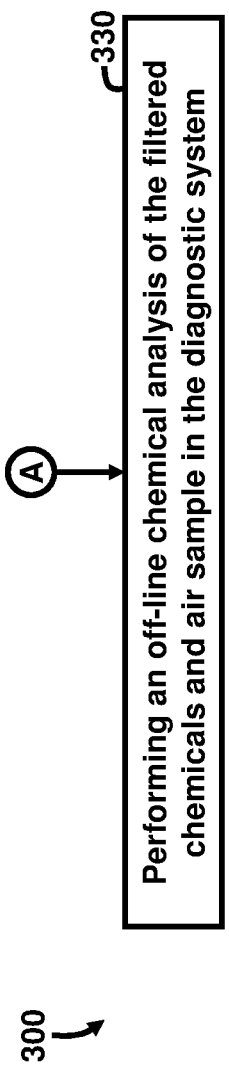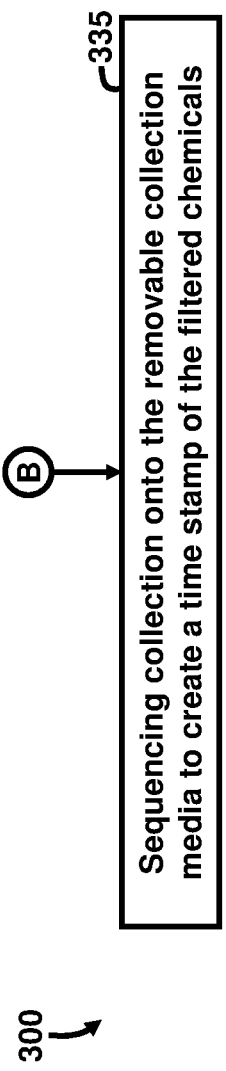

AIRCRAFT AIR QUALITY TESTING SYSTEM

CROSS-REFERENCE TO RELATED APPLICATION(S)

This application claims the benefit of U.S. Provisional Patent Application No. 62/664,405 filed on Apr. 30, 2018, which is incorporated herein by reference in its entirety.

GOVERNMENT INTEREST

The invention described herein may be manufactured and used by or for the Government of the United States for all government purposes without the payment of any royalty.

BACKGROUND

Field of the Invention

The embodiments herein generally relate to diagnostic systems for testing air quality, and more particularly to diagnostic systems for testing air quality in vehicles such as aircraft with an on-board oxygen generating system (OBOGS).

Background of the Invention

There is a recurring phenomenon where advanced military aircraft pilots experience symptoms of degraded health and performance during flight. This phenomenon, commonly referred to as unexplained physiological events, has led to the grounding of the F-22, F-35, and Air Force Trainer fleets. Chemical contamination in pilot breathing air has been identified as a potential contributor to unexplained physiological events experienced by pilots. There is currently no standardized approach to monitor air quality during engine runs in aircraft. However, a diagnostic system that is capable of monitoring and analyzing air that is supplied to pilots would help assess the cause of the unexplained physiological events experienced by pilots.

BRIEF SUMMARY OF THE INVENTION

In view of the foregoing, an embodiment herein provides an aircraft air quality testing system comprising a portable housing unit to be removably placed within an aircraft; an air testing unit secured inside the portable housing unit, the air testing unit comprising: a sampling unit to receive an air sample during a plurality of oxygen generation system cycles and engine thrust settings of the aircraft; a mass flow meter to monitor real-time flow rate of the air sample entering the sampling unit; a removable collection media to receive the air sample from the sampling unit; a plurality of analyzers to perform a real-time chemical analysis of the air sample. The chemical analysis may refer to gas, vapor, and aerosol chemicals, wherein analyzers for the gases and vapors may operate independently from the analyzers for aerosols or particles. The system further comprises a first computer operatively connected to the portable housing unit, the first computer comprising: a processor to receive the real-time chemical analysis and flow rate and generate real-time chemical analysis and flow rate data; a memory device to store the real-time chemical analysis and flow rate data; and a display device operatively connected to the portable housing unit, wherein the display device is to output the real-time chemical and flow rate analysis data.

The air testing unit may be directly connected to a first oxygen generation system breathing line of the aircraft. The air testing unit may collect ambient air from the aircraft or from a second oxygen generation system breathing line of the aircraft. The memory device may comprise a removable memory device to connect to a second computer to perform an off-line analysis based on the real-time flow rate and chemical analysis data. The first computer may comprise a tablet computer that is positioned on an outer surface of the portable housing unit. The mass flow meter and plurality of analyzers may be fully disposed in the portable housing unit. The system may comprise a pump to pull a controlled volume of air over the collection media; an air flow controller to direct the air sample in the air testing unit. The system may comprise a valve to control a flow of air in the air testing unit. The system may comprise a power supply operatively connected to the air testing unit and the first computer.

Another embodiment provides a portable air quality measurement device comprising a plurality of sensors to receive a plurality of air samples from within a vehicle that generates engine exhaust; a plurality of collection mechanisms to filter chemicals from the plurality of air samples; a processing unit to perform a real-time chemical analysis of the plurality of air samples; and a display device operatively connected to the processing unit to display the real-time chemical analysis. The device may comprise a plurality of transducers operatively connected to the plurality of collection mechanisms, wherein the plurality of transducers controls the operation of the plurality of collection mechanisms. The device may comprise an air flow controller to direct the plurality of air samples to the plurality of collection mechanisms, wherein each of the plurality of collection mechanisms are configured to collect a separate air sample.

The air flow controller may direct a flow of air of the plurality of air samples of at least 10 LPM (liters per minute). The plurality of air samples may comprise a first air sample from a first oxygen generation system breathing line of the vehicle and a second air sample comprising ambient air from inside the vehicle. The processing unit may simultaneously perform the real-time chemical analysis of both the first air sample and the second air sample. The plurality of sensors may sense oxygen concentration levels in the range of approximately 21-96%.

Another embodiment provides a method of measuring air quality, the method comprising: receiving an air sample in a portable air quality measurement device on-board a vehicle; selectively controlling a flow of the air sample in the portable air quality measurement device; performing a real-time chemical analysis of the air sample and filtered chemicals in the portable air quality measurement device; displaying real-time chemical analysis and flow rate data comprising the real-time chemical analysis on a portable display device in the vehicle; and transferring the real-time chemical analysis and flow rate data to a diagnostic system remotely located from the vehicle. The air sample may be provided during a plurality of oxygen generation system cycles and engine thrust settings of the vehicle. The method may comprise performing an off-line chemical analysis of the filtered chemicals and air sample in the diagnostic system. The chemicals may be filtered from the air sample in a plurality of removable collection media of the portable air quality measurement device. The method may further comprise sequencing collection onto the removable collection media to create a time stamp of the filtered chemicals. The real-time chemical analysis may comprise an analysis of levels of carbon monoxide, carbon dioxide, nitrogen oxide, nitrogen dioxide, sulfur dioxide, oxygen, volatile organic compounds, ozone, ultrafine particles, relative humidity, air pressure, temperature, and mass flow rate of the air sample.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 16 is a flow diagram illustrating the method of FIG. 15 performing an off-line chemical analysis, according to an embodiment herein; and FIG. 17 is a flow diagram illustrating the method of FIG. 15 sequencing collection of chemicals, according to an embodiment herein.

DETAILED DESCRIPTION OF THE INVENTION

Figure 1:
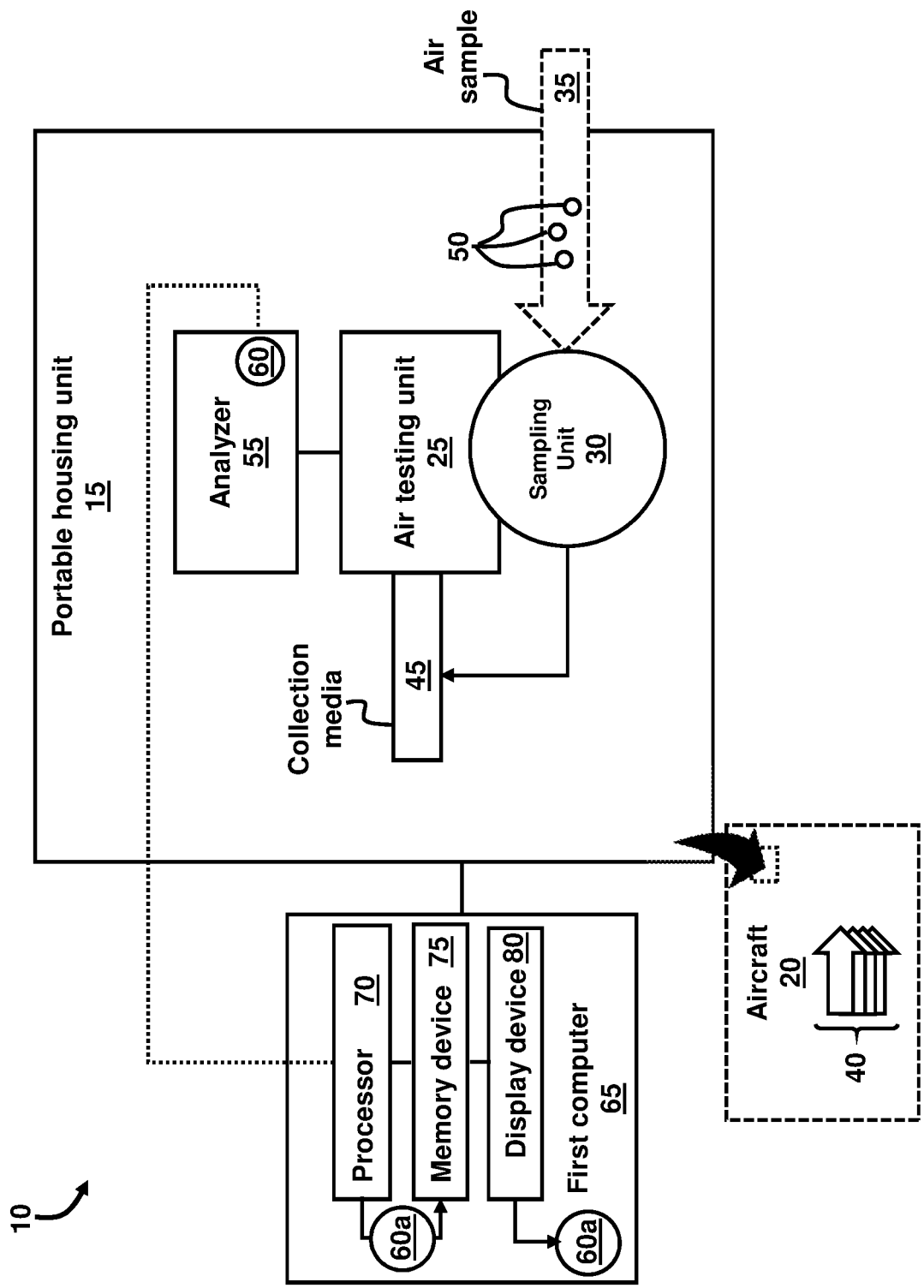
FIG. 1 is a block diagram illustrating an aircraft air quality testing system, according to an embodiment herein.

Embodiments of the disclosed invention, its various features and the advantageous details thereof, are explained more fully with reference to the non-limiting embodiments that are illustrated in the accompanying drawings and detailed in the following description. Descriptions of well-known components and processing techniques are omitted to not unnecessarily obscure what is being disclosed. Examples may be provided and when so provided are intended merely to facilitate an understanding of the ways in which the invention may be practiced and to further enable those of skill in the art to practice its various embodiments. Accordingly, examples should not be construed as limiting the scope of what is disclosed and otherwise claimed.

According to various examples, the embodiments herein provide a portable air testing device to characterize chemical (gas, vapor, and aerosol) contaminants during engine ground runs for advanced aircraft to enable rapid characterization of oxygen concentrations and diagnosis of chemical contamination in breathing air in the aircraft. The device comprises several real-time chemical and environmental sensors packaged within analyzers and collection methods for comprehensive analysis of potential chemical contaminants in a heavy-duty portable housing case. The exterior of the case includes connections for sampling directly from the pilot air supply, as well as the aircraft cabin ambient air, simultaneously. Breathing air is subject to programmed or user-controlled sampling during various engine thrust cycles and oxygen settings. The sampled air is delivered to a gas sensor suite and particle sensing unit for real-time monitoring and sorbed or deposited on collection media for off-line chemical analysis. The flow rate of air supplied directly to the pilot is also monitored throughout the sampling period to check for pressure and flow rate swings during engine thrust and oxygen concentration changes. Real-time data are saved into text files and displayed on a tablet computer attached to the housing case. The diagnostic components may be shielded within the heavy-duty portable case suitable for use within the cockpit. The case may have a custom-designed interior to secure all instruments and hardware. The case's exterior may include connections for sampling directly from the air supply for the pilot's mask, as well as the cabin's ambient air, simultaneously, or alternatively, in a two-seater cockpit, the samples could be collected from both pilot air supplies.

Referring now to the drawings, and more particularly to FIGS. 1 through 17, where similar reference characters denote corresponding features consistently throughout, there are shown exemplary embodiments. In the drawings, the size and relative sizes of components, layers, and regions may be exaggerated for clarity.

FIG. 1 illustrates an aircraft air quality testing system 10 comprising a portable housing unit 15 to be removably placed within an aircraft 20. The portable housing unit 15 may be configured in any suitable size or shape, and may be made of any durable material including metal, wood, rubber, or plastic. In an example, the portable housing unit 15 may comprise a manifold (not shown) to operatively connect the various components contained in the portable housing unit 15. For example, the manifold may comprise stainless steel material in order to prevent internal contamination introduction in the portable housing unit 15. In an example, the portable housing unit 15 may be configured as a box approximately 15"×13"×10", although other shapes and dimensions are possible, and the embodiments herein are not restricted to any particular configuration. The portable housing unit 15 is configured to be easily transferrable inside/outside the aircraft 20 by a user without the need of any special-purpose equipment or system for lifting or transfer thereof. The aircraft 20 may be any type of aircraft vehicle including commercial, personal, and military aircraft.

The aircraft air quality testing system 10 also comprises an air testing unit 25 secured inside the portable housing unit 15. In an example, the air testing unit 25 may be completely secured inside the portable housing unit 15, and in another example the air testing unit 25 may be partially secured inside the portable housing unit 15. The air testing unit 25 comprises a sampling unit 30 to receive an air sample 35 during a plurality of oxygen generation system (e.g., OBOGS) cycles or engine thrust settings 40 of the aircraft 20. In an example, the sampling unit 30 may comprise a gas sensor such as a chemical microsensor. According to an example, the sampling unit 30 may comprise a sensing element that detects a chemical reaction associated with a measurand to be detected by the sampling unit 30 such that the sensing element physically transforms based on the chemical reaction. The change in physical state of the sensing element is detected by a transducer, which then creates an electrical signal that is transmitted to electrical circuitry to generate a sensor signal containing the data associated with the measurands detected by the sampling unit 30. For example, the sampling unit 30 may be configured to detect various environmental measurands such as humidity, temperature, pressure, relative humidity, gases, vapors, aerosols, among other measurands. The plurality of oxygen generation system cycles and engine thrust settings 40 may produce oxygen enriched air for one or more pilots in the aircraft 20.

The air testing unit 25 further comprises a removable collection media 45 to receive the air sample 35 from the sampling unit 30. In an example, the removable collection media 45 may comprise any suitable type of collection media such as filter material, thermal desorption tubes, and canisters, among other types of collection media, which are each connected to a sampling pump to ensure a controlled volume of air over the media. Moreover, the collection media 45 is removable from the air testing unit 25 to permit replacement of the collection media 45 after testing has been completed. The air sample 35 may be collected from the ambient air inside the aircraft 20, and more particularly, from inside the cockpit of the aircraft 20. Moreover, the air sample 35 may be collected from the oxygen enriched air provided during the plurality of oxygen generation system cycles and engine thrust settings 40. The targeted chemicals 50 may be based on a predetermined set of chemicals which comprise unique chemical signatures that are to be detected by the sampling unit 30.

The air testing unit 25 further comprises a plurality of analyzers 55 to perform a real-time chemical analysis 60 of the air sample 35 and the filtered targeted chemicals 50. Furthermore, the real-time chemical analysis 60 of the air sample 35 may occur while the air testing unit 25 is on-board the aircraft 20, in an example such that the plurality of analyzers 55 conducts the real-time chemical analysis 60 and outputs the results as the air sample 35 with the targeted chemicals 50 are collected. In an example, the plurality of analyzers 55 may be fully disposed in the portable housing unit 15. In another example, the plurality of analyzers 55 may be partially disposed in the portable housing unit 15. Moreover, the plurality of analyzers 55 may be removably attached from the portable housing unit 15 according to an example.

The aircraft air quality testing system 10 also comprises a first computer 65 operatively connected to the portable housing unit 15. The first computer 65 may be a standalone computing device or may be communicatively linked to a server. The first computer 65 may comprise a tablet computer, smartphone, or any other compact computing device. Moreover, the first computer 65 is operatively connected to the air testing unit 25. The first computer 65 may be operatively connected to the plurality of analyzers 55. Furthermore, the first computer 65 comprises a processor 70 to receive the real-time chemical analysis 60 in the form of real-time chemical analysis and flow rate data 60a, and store the real-time chemical analysis and flow rate data 60a.

In some examples, the processor 70 described herein and/or illustrated in the figures may include hardware-enabled modules and may include a plurality of overlapping or independent electronic circuits, devices, and discrete elements packaged onto a circuit board to provide data and signal processing functionality within the first computer 65. An example might be a comparator, inverter, or flip-flop, which could include a plurality of transistors and other supporting devices and circuit elements. The modules that include electronic circuits may process computer logic instructions capable of providing digital and/or analog signals for performing various functions as described herein. The various functions can further be physically saved as any of data structures, data paths, data objects, data object models, object files, and database components. For example, the data objects could include a digital packet of structured data. The data structures could include any of an array, tuple, map, union, variant, set, graph, tree, node, and an object, which may be stored and retrieved by computer memory device 75 and may be managed by processors, compilers, and other computer hardware components. The data paths may be part of a computer central processing unit (CPU) that performs operations and calculations as instructed by the computer logic instructions. The data paths could include digital electronic circuits, multipliers, registers, and buses capable of performing data processing operations and arithmetic operations (e.g., Add, Subtract, etc.), bitwise logical operations (AND, OR, XOR, etc.), bit shift operations (e.g., arithmetic, logical, rotate, etc.), and complex operations (e.g., using single clock calculations, sequential calculations, iterative calculations, etc.). The data objects may be physical locations in the computer memory device 75 and can be a variable data object, a data structure, or a function. In an example of a relational database, the data objects can be set as a table or column. Other implementations include specialized objects, distributed objects, object-oriented programming objects, and semantic web objects, for example. Furthermore, the data object models can be set as an application programming interface for creating HyperText Markup Language (HTML) and Extensible Markup Language (XML) electronic documents. The models can be further set as any of a tree, graph, container, list, map, queue, set, stack, and variations thereof, according to various examples. The data object files may be created by compilers and assemblers and may contain generated binary code and data for a source file. The database components can include any of tables, indexes, views, stored procedures, and triggers.

The processor 70 may comprise any of an integrated circuit, an application specific integrated circuit (ASIC), field-programmable gate array (FPGA), and a microcontroller according to exemplary embodiments. In some examples, the processor 70 may comprise a CPU of the first computer 65. In other examples the processor 70 may be a discrete component independent of other processing components in the first computer 65. In other examples, the processor 70 may be a microprocessor, microcontroller, hardware engine, hardware pipeline, and/or other hardware-enabled device suitable for receiving, processing, operating, and performing various functions required by the first computer 65. The processor 70 may be provided in the first computer 65, coupled to the first computer 65, or communicatively linked to the first computer 65 from a remote networked location, according to various examples.

The memory device 75 of the first computer 65 is to store the real-time chemical analysis and flow rate data 60*a*. In an example, the memory device 75 may be random access memory (RAM) of the first computer 65, or any other suitable storage media communicatively linked to the first computer 65. Additionally, the first computer 65 comprises a display device 80 operatively connected to the portable housing unit 15. The display device 80 is to output the real-time chemical analysis and flow rate data 60*a*. The display device 80 may be a liquid crystal display (LCD) according to an example or any type of monitor, screen, or other visual output capable of outputting and presenting data. In some examples, the output of the display device 80 may comprise a visual output and/or an audio output by a speaker connected to the display device 80. Moreover, the output of the real-time chemical analysis and flow rate data 60*a* may be in the form of any of graphs, charts, tables, alphanumeric sequences, codes, symbols, colors, sounds, images, and video, for example.

Figure 2:
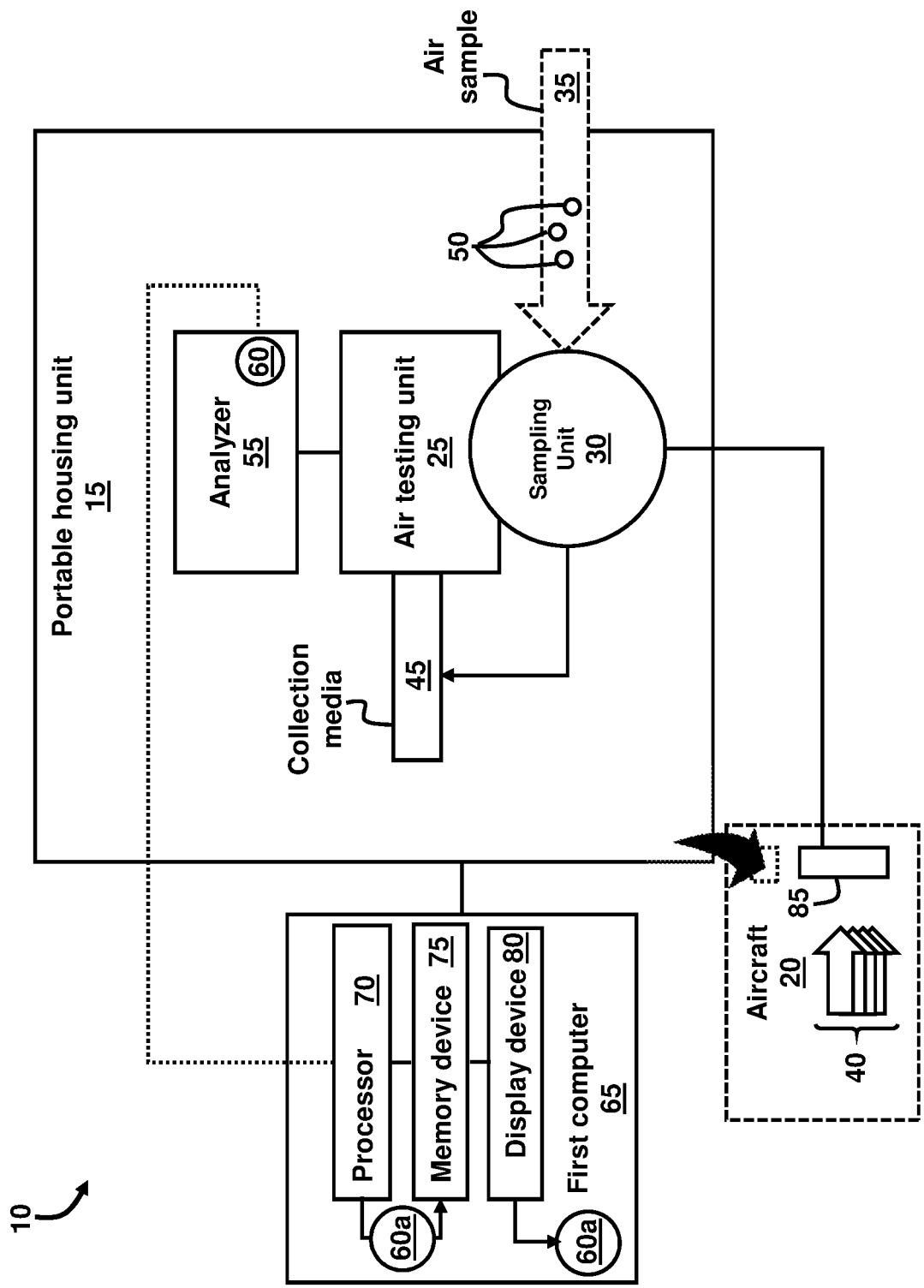
FIG. 2 is a block diagram illustrating the aircraft air quality testing system of FIG. 1 with the sensor connected to the first oxygen generation system breathing line, according to an embodiment herein.

FIG. 2, with reference to FIG. 1, illustrates that the air testing unit 25 is directly connected to a first oxygen generation system breathing line 85 of the aircraft 20. In an example, the first oxygen generation system breathing line 85 may be configured to carry and transmit the oxygen enriched air, which contains the air sample 35, provided during the plurality of oxygen generation system cycles and engine thrust settings 40 to a pilot's mask in the aircraft 20. The direct connection of the air testing unit 25 to the first oxygen generation system breathing line 85 may ensure that the air testing unit 25 is permitted to detect the air sample 35 without interference with any other area or component of the aircraft 20. In another example, the air testing unit 25 may be indirectly connected to the first oxygen generation system breathing line 85 with an intervening component, valve, etc. connected therebetween. The first oxygen generation system breathing line 85 may comprise tubing, coils, pipes, or any other type of conduit capable of carrying and transmitting the oxygen enriched air to an air/breathing mask of a first pilot in the aircraft 20.

Figure 3:
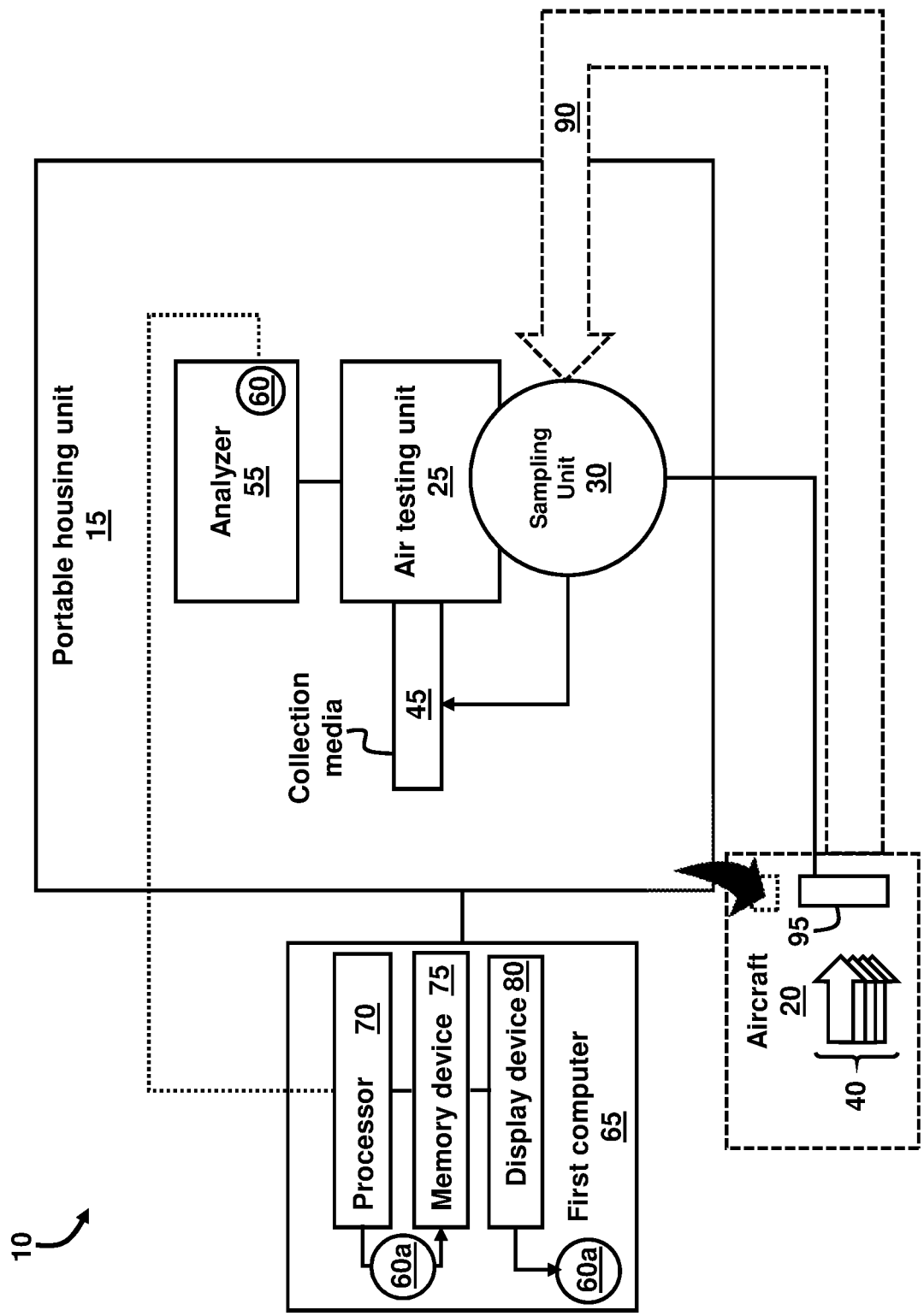
FIG. 3 is a block diagram illustrating the aircraft air quality testing system of FIG. 2 with the sensor collecting ambient air from the aircraft or from a second oxygen generation system breathing line, according to an embodiment herein.

FIG. 3, with reference to FIGS. 1 and 2, illustrates that the air testing unit 25 is to collect ambient air 90 from the aircraft 20 or from a second oxygen generation system breathing line 95 of the aircraft 20 in the event the aircraft 20 has two pilots. In an example, the ambient air 90 may be collected from the cockpit of the aircraft 20. The second oxygen generation system breathing line 95 may comprise tubing, coils, pipes, or any other type of conduit capable of carrying and transmitting the oxygen enriched air to a mask of a second pilot in the aircraft 20.

Figure 4:
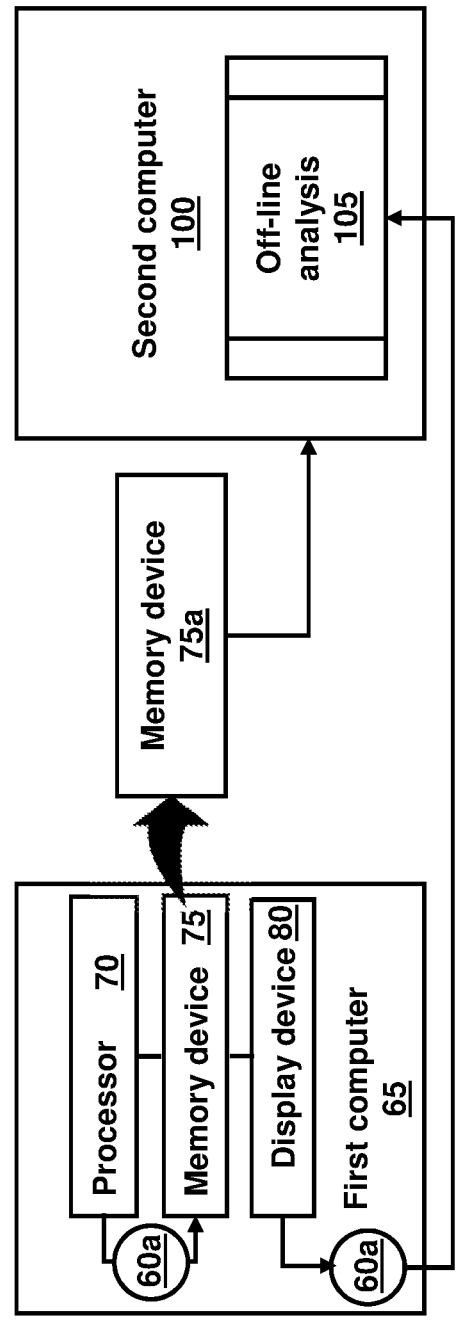
FIG. 4 is a block diagram illustrating aspects of the memory of the aircraft air quality testing system of FIG. 1 with a second computer, according to an embodiment herein.

FIG. 4, with reference to FIGS. 1 through 3, illustrates that the memory device 75 comprises a removable memory device 75*a* to connect to a second computer 100 to perform an off-line analysis 105 based on the real-time chemical analysis and flow rate data 60*a*. According to some examples, the removable memory device 75*a* may include a universal serial bus (USB) flash drive, a memory card, a memory stick, an external hard disk drive, or any other memory storage device capable of being removeable from the first computer 65 and attached or linked to the second computer 100. According to some examples, the second computer 100 may be a standalone computing device or may be communicatively linked to a server or may be part of a computer system with a plurality of computers. The second computer 100 may comprise a tablet computer, smartphone, desktop computer, laptop computer, a server, or any other type of computing device. This may permit the real-time chemical analysis and flow rate data 60*a* to be transferred from the first computer 65 to the second computer 100 such that the second computer 100 may perform analysis of the real-time chemical analysis and flow rate data 60*a* or may use the real-time chemical analysis and flow rate data 60*a* to perform analysis with other data. In an example, the first computer 65 and the second computer 100 are positioned in different locations such that the first computer 65 is attached or proximately located to the portable housing unit 15 and the second computer 100 is not attached or proximately located to the portable housing unit 15. Furthermore, the second computer 100 may be located in a different facility or location apart from the aircraft 20. In another example, the first computer 65 and the second computer 100 may be communicatively linked to one another such as through wireless connection to permit transfer of the real-time chemical analysis and flow rate data 60 from the first computer 65 and the second computer 100 without the intervening removable memory device 75*a*. In some examples, the off-line chemical analysis 105 may involve further or enhanced analysis of the real-time chemical analysis 60 performed by the portable air quality measurement device 200 itself. Moreover, the off-line chemical analysis 105 may include analysis such as spectroscopy, mass spectrometry, electrochemistry, calorimetry, chromatography, and microscopy, among other analysis techniques of the air sample 35.

Figure 5:
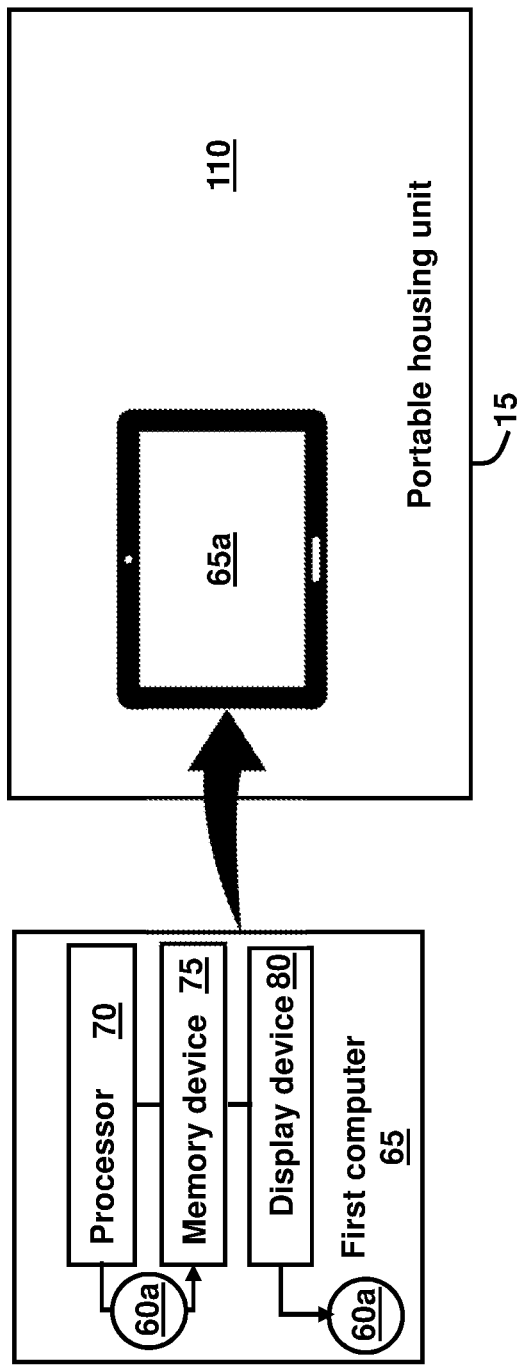
FIG. 5 is a block diagram illustrating an example of the first computer of the aircraft air quality testing system of FIG. 1 configured as a tablet computer, according to an embodiment herein.

FIG. 5, with reference to FIGS. 1 through 4, illustrates that the first computer 65 comprises a tablet computer 65*a* that is positioned on an outer surface 110 of the portable housing unit 15. The tablet computer 65*a* may be ruggedized and may be any suitable size and configuration capable of fitting on outer surface 110 of the portable housing unit 15. The position of the tablet computer 65*a* on the outer surface 110 of the portable housing unit 15 permits a user to easily review the real-time chemical analysis and flow rate data 60 displayed on the tablet computer 65*a* (e.g., the display device 80 of the tablet computer 65*a*). The tablet computer 65*a* may be removable from the portable housing unit 15 and may comprise attachment mechanisms to removably attached/detach the tablet computer 65*a* to/from the outer surface 110 of the portable housing unit 15.

Figure 6:
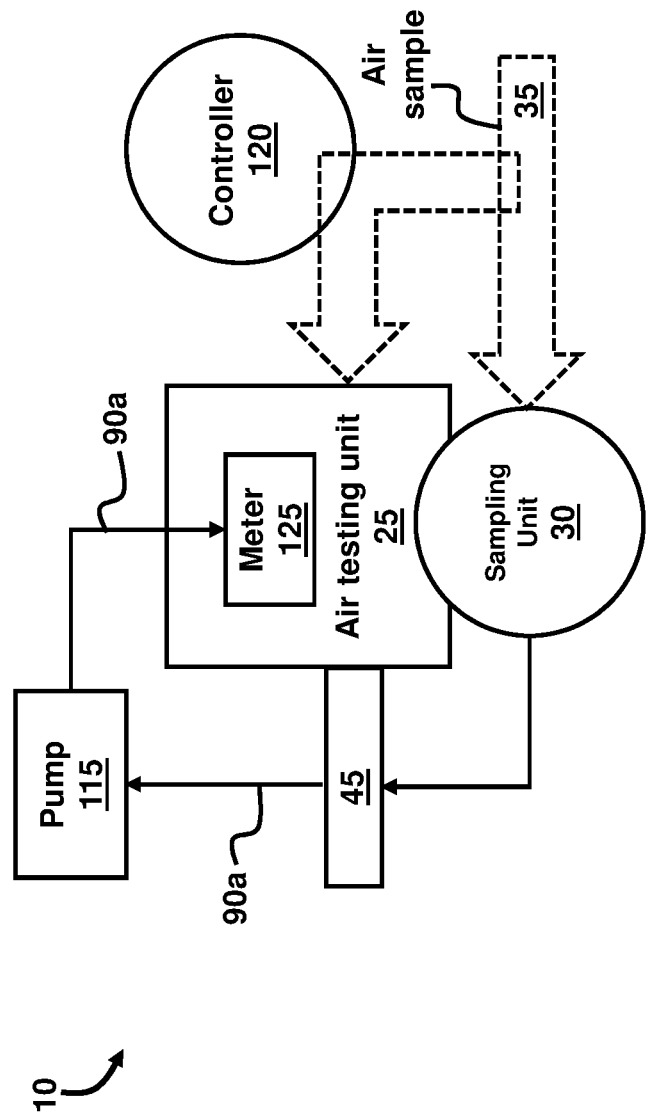
FIG. 6 is a block diagram illustrating the aircraft air quality testing system of FIG. 1 with a pump, an air flow controller, and a mass flow meter, according to an embodiment herein.

FIG. 6, with reference to FIGS. 1 through 5, illustrates that the aircraft air quality testing system 10 comprises a pump or series of pumps 115 to pull a controlled volume of air 90*a* over the collection media 45. The pump 115 may be any type of pump that interacts with the ambient air 90 in order to pull the controlled volume of air 90*a* taken from the ambient air 90 over the collection media 45. The pump 115 may be a pneumatic pump, electrical pump, electro-mechanical pump, mechanical pump, or a combination thereof, according to various examples. The pump 115 may be positioned in the portable housing unit 15 or may be outside of the portable housing unit 15, or may be partially in/out of the portable housing unit 15 according to some examples. In an example, the ambient air 90 may be air in the cockpit of the aircraft 20. The controlled volume of air 90a may be a portion of the ambient air 90 pulled by the pump 115. In an example, the air sample 35 may be a portion of the ambient air 90 to be tested for the targeted chemicals 50. In other examples, the air sample 35 may be derived from the first oxygen generation system breathing line 85 or the second oxygen generation system breathing line 95, as described above in FIGS. 2 and 3.

The aircraft air quality testing system 10 may also include an air flow controller 120, which may be part of the pump 115, to direct the air sample 35 in the air testing unit 25. In some examples, the air flow controller 120 may comprise an electrical device, magnetic device, electro-mechanical device, mechanical device, pneumatic device, or a combination thereof. The air flow controller 120 may control the mass flow rate of the air sample 35 in the air testing unit 25, and may be operatively connected to the pump 115, in an example. In another example, the air flow controller 120 may comprise a fan to change the mass flow rate of the air sample 35 in the air testing unit 25 based on user input or a predetermined threshold for the mass flow rate of the air sample 35. The air flow controller 120 may be positioned in the portable housing unit 15 or may be outside of the portable housing unit 15, or may be partially in/out of the portable housing unit 15 according to some examples.

The aircraft air quality testing system 10 also includes an mass flow meter 125 to monitor the flow of air 90a in the air testing unit 25. In an example, the mass flow meter 125 may be operatively connected to any of the pump 115 and the air flow controller 120. The mass flow meter 125 may measure the mass flow rate of the flow of air 90a in the air testing unit. The operations of any of the pump 115, air flow controller 120, and mass flow meter 125 may be controlled by the processor 70 of the first computer 65, according to an example. In other examples, the operations of any of the pump 115, air flow controller 120, and mass flow meter 125 may be independently controlled based on preprogrammed instructions and settings associated with the pump 115, air flow controller 120, and mass flow meter 125. Alternatively, any of the pump 115, air flow controller 120, and mass flow meter 125 may be controlled by a user. The mass flow meter 125 may be positioned in the portable housing unit 15 or may be outside of the portable housing unit 15, or may be partially in/out of the portable housing unit 15 according to some examples.

Figure 7:
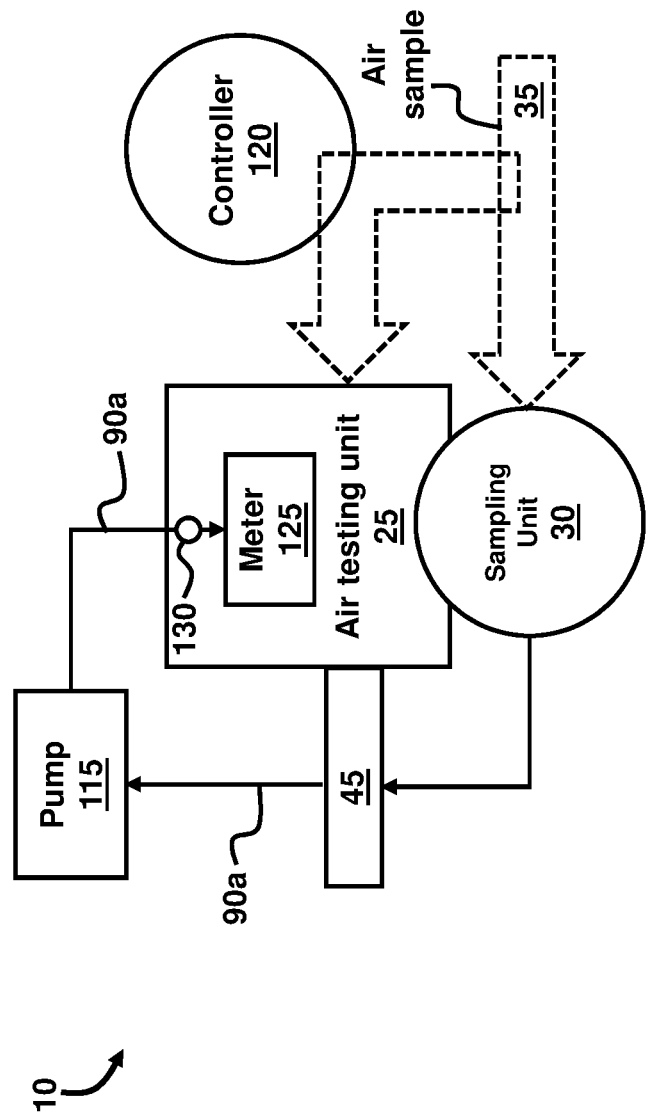
FIG. 7 is a block diagram illustrating the aircraft air quality testing system of FIG. 1 with a valve, according to an embodiment herein.

FIG. 7, with reference to FIGS. 1 through 6, illustrates that the aircraft air quality testing system 10 comprises a series of valves 130 to control a flow of air 90a in the air testing unit 25. The valves 130 are to direct the flow path to separate sets of collection media during different oxygen system regulator or engine thrust settings. The valves 130 may comprise a pneumatic valve, electrical valve, mechanical valve, electro-mechanical valve, magnetic valve, or a combination thereof. The valves 130 may be operatively connected to any of the pump 115, air flow controller 120, and mass flow meter 125. Moreover, the operations of the valves 130 may be controlled by the processor 70 of the first computer 65, according to an example, or may be independently controlled based on preprogrammed instructions and settings associated with the valves 130. Alternatively, the valves 130 may be controlled by a user. The valves 130 may be positioned in the portable housing unit 15 or may be outside of the portable housing unit 15, or may be partially in/out of the portable housing unit 15 according to some examples.

Figure 8:
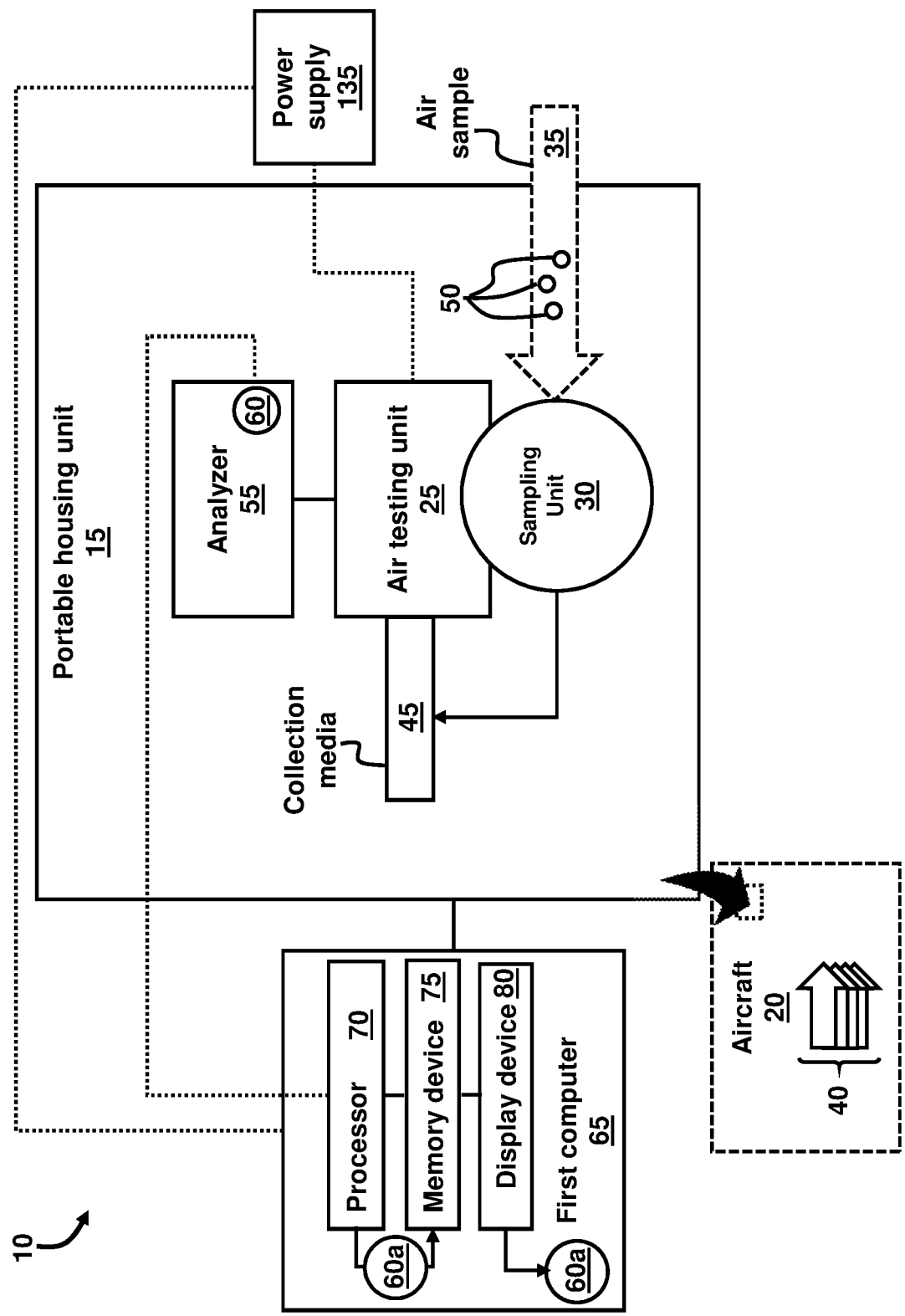
FIG. 8 is a block diagram illustrating the aircraft air quality testing system of FIG. 1 with a power supply, according to an embodiment herein.

FIG. 8, with reference to FIGS. 1 through 7, illustrates that the aircraft air quality testing system 10 comprises a power supply 135 operatively connected to the air testing unit 25 and the first computer 65. The power supply 135 may be a rechargeable battery in an example. The power supply 135 provides power to the air testing unit 25 and the first computer 65 according to an example. Additionally, in some examples, the power supply 135 may provide power to any of the pumps 115, air flow controller 120, mass flow meters 125, and valves 130. Furthermore, the power supply 135 may provide power to the plurality of analyzers 55, according to other examples.

Figure 9:
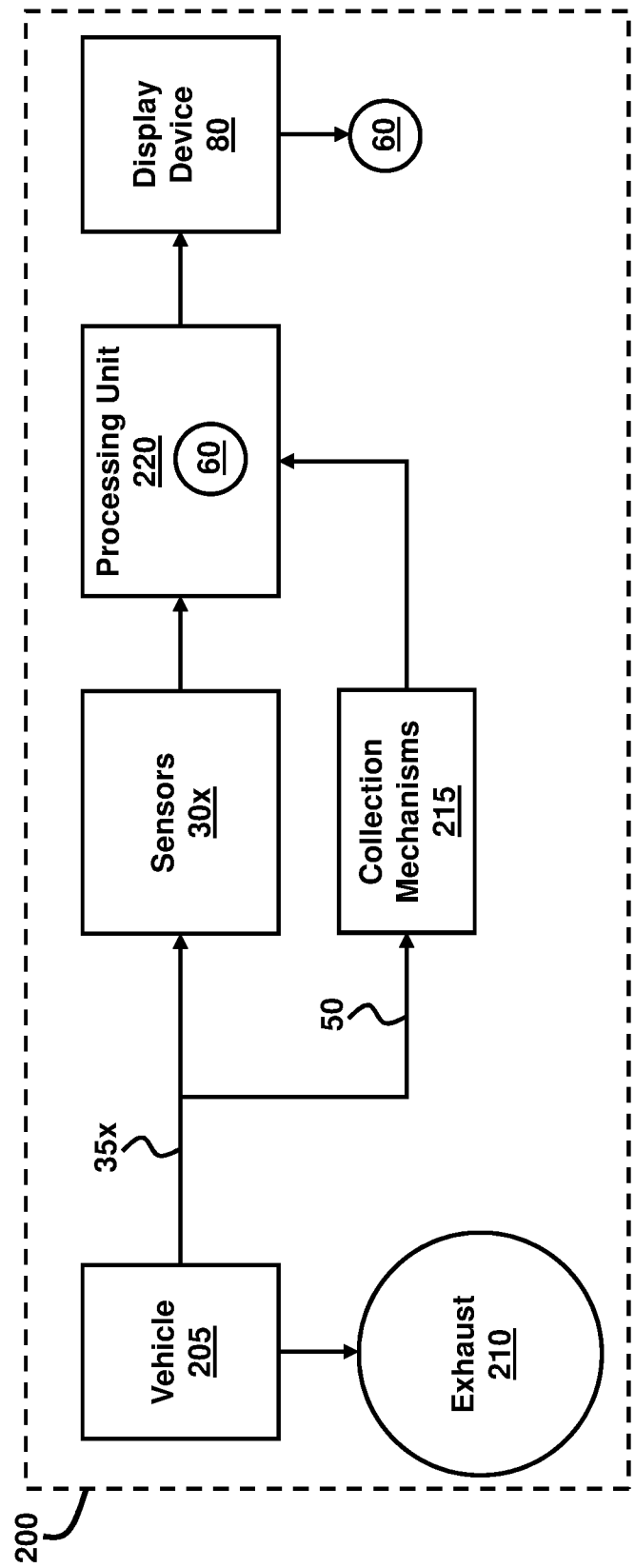
FIG. 9 is a block diagram illustrating a portable air quality measurement device, according to an embodiment herein.

FIG. 9, with reference to FIGS. 1 through 8, illustrates a portable air quality measurement device(s) 200, which may be configured as chemical analyzers, and comprising a plurality of sensors $30x$, such as electrochemical, infrared, photoionization, electrometer, optical or others, to receive a plurality of air samples $35x$ from within a vehicle 205. The device 200 may be configured in any suitable size or shape, and may be made of any durable material including metal, wood, rubber, or plastic. In an example, the device 200 may be configured as a box approximately 15"×13"×10", although other shapes and dimensions are possible, and the embodiments herein are not restricted to any particular configuration. The device 200 is configured to be easily transferrable inside/outside the vehicle 205 by a user without the need of any special-purpose equipment or system for lifting or transfer thereof. The vehicle 205 may be any type of vehicle including commercial, personal, and military vehicles. Moreover, the vehicle 205 may comprise aircraft, aerospace, or aeronautical vehicles, according to some examples.

According to an example, the plurality of sensors $30x$ may each comprise a sensing element that detects a chemical reaction associated with a measurand to be detected such that the sensing element physically transforms based on the chemical reaction. The change in physical state of the sensing element is detected by a transducer, which then creates an electrical signal that is transmitted to electrical circuitry to generate a sensor signal containing the data associated with the measurands. For example, the plurality of sensors $30x$ may be configured to detect various environmental measurands such as relative humidity, temperature, pressure, gas and vapor concentrations, particle concentrations, among other measurands. According to an example, each of the plurality of sensors $30x$ may be configured to detect a different measurand compared to the other sensors $30x$ such that each of the plurality of sensors $30x$ may be uniquely configured in order to detect a unique measurand. The plurality of air samples $35x$ may be collected from the ambient air inside the vehicle 205, and in one example, from inside the cockpit of the vehicle 205. In an example, one of the sensors $30x$ senses oxygen concentration levels in the range of approximately 21-96%.

According to various examples, the engine exhaust 210 may contain any type of exhaust fumes and may be generated by any type of engine capable of generating engine exhaust 210 and which is capable of entering the inside of the vehicle 205. Engine bleed air from the compressor stages of the engine are used to pressurize the environmental control system, and subsequently, the OBOGS. Chemical contaminants could come from engine exhaust that is reentrained, but could also come from partially combusted aircraft fluids that leak into the system (the partial combustion is due to the high temperatures within the engine, but are not necessarily components in jet exhaust). In an example, the engine exhaust 210 may comprise aircraft engine exhaust containing carbon dioxide, sulfur oxide, nitrogen oxide, carbon monoxide, nitric oxide, sulfur dioxide, nitrogen dioxide, oxygen, and any volatile organic compounds. The vehicle 205 may be configured to inadvertently allow the engine exhaust 210 to enter the driver/passenger compartment of the vehicle 205, such as the cockpit of an aircraft causing the engine exhaust 210 to mix with the breathing line air and/or the ambient air of the driver(s) or pilot(s), etc.

The portable air quality measurement device 200 also comprises a plurality of collection mechanisms 215 to filter chemicals 50 from the plurality of air samples 35$x$. In an example, the plurality of collection mechanisms 215 may comprise any suitable type of collection mechanisms such as filter cassettes, thermal desorption tube, and canisters, among other types of collection mechanisms. Moreover, the plurality of collection mechanisms 215 may be removable from the portable air quality measurement device 200 to permit removal and replacement of the plurality of collection mechanisms 215 after testing has been completed.

The portable air quality measurement device 200 also comprises a processing unit 220 to perform a real-time chemical analysis 60 of the plurality of air samples 35$x$. The processing unit 220 may be configured as a hardware component of the portable air quality measurement device 200 or the processing unit 220 may be remotely located as part of a separate computing system and/or server and may be communicatively linked to the portable air quality measurement device 200 such as through wireless communication, for example. In some examples, the processing unit 220 described herein and/or illustrated in the figures may include hardware-enabled modules and may include a plurality of overlapping or independent electronic circuits, devices, and discrete elements packaged onto a circuit board to provide data and signal processing functionality within the portable air quality measurement device 200. An example might be a comparator, inverter, or flip-flop, which could include a plurality of transistors and other supporting devices and circuit elements. The modules that include electronic circuits may process computer logic instructions capable of providing digital and/or analog signals for performing various functions as described herein. The various functions can further be physically saved as any of data structures, data paths, data objects, data object models, object files, and database components. For example, the data objects could include a digital packet of structured data. The data structures could include any of an array, tuple, map, union, variant, set, graph, tree, node, and an object, which may be stored and retrieved by computer memory and may be managed by processors, compilers, and other computer hardware components. The data paths may be part of a computer CPU that performs operations and calculations as instructed by the computer logic instructions. The data paths could include digital electronic circuits, multipliers, registers, and buses capable of performing data processing operations and arithmetic operations (e.g., Add, Subtract, etc.), bitwise logical operations (AND, OR, XOR, etc.), bit shift operations (e.g., arithmetic, logical, rotate, etc.), and complex operations (e.g., using single clock calculations, sequential calculations, iterative calculations, etc.). The data objects may be physical locations in the computer memory and can be a variable data object, a data structure, or a function. In an example of a relational database, the data objects can be set as a table or column. Other implementations include specialized objects, distributed objects, object-oriented programming objects, and semantic web objects, for example. Furthermore, the data object models can be set as an application programming interface for creating HTML and XML electronic documents. The models can be further set as any of a tree, graph, container, list, map, queue, set, stack, and variations thereof, according to various examples. The data object files may be created by compilers and assemblers and may contain generated binary code and data for a source file. The database components can include any of tables, indexes, views, stored procedures, and triggers.

The processing unit 220 may comprise any of an integrated circuit, an ASIC, FPGA, and a microcontroller according to exemplary embodiments. In some examples, the processing unit 220 may comprise a CPU of the portable air quality measurement device 200. In other examples the processing unit 220 may be a discrete component independent of other processing components in the portable air quality measurement device 200. In other examples, the processing unit 220 may be a microprocessor, microcontroller, hardware engine, hardware pipeline, and/or other hardware-enabled device suitable for receiving, processing, operating, and performing various functions required by the portable air quality measurement device 200. The processing unit 220 may be provided in the portable air quality measurement device 200, coupled to the portable air quality measurement device 200, or communicatively linked to the portable air quality measurement device 200 from a remote networked location, according to various examples.

In some examples, the processing unit 220 may perform several different types of techniques for the real-time chemical analysis 60 such as spectroscopy, mass spectrometry, electrochemistry, calorimetry, chromatography, and microscopy, among other techniques. Furthermore, the real-time chemical analysis 60 of the plurality of air samples 35$x$ may occur while the portable air quality measurement device 200 is on-board the vehicle 205, in an example such that the processing unit 220 conducts the real-time chemical analysis 60 and outputs the results as the plurality of air samples 35$x$ with the filtered chemicals 50 are collected and suitably processed by the processing unit 220.

The portable air quality measurement device 200 also comprises a display device 80 operatively connected to the processing unit 220 to display the real-time flow rate and chemical analysis 60. In an example, the display device 80 may be removably attached to the outside of the portable air quality measure device 200. The display device 80 is to output the results of the real-time flow rate and chemical analysis 60. The display device 80 may be a LCD according to an example or any type of monitor, screen, or other visual output capable of outputting and presenting data. In some examples, the output of the display device 80 may comprise a visual output and/or an audio output by a speaker connected to the display device 80. Moreover, the output of the results of the real-time flow rate and chemical analysis 60 may be in the form of any of graphs, charts, tables, alphanumeric sequences, codes, symbols, colors, sounds, images, and video, for example.

Figure 10:
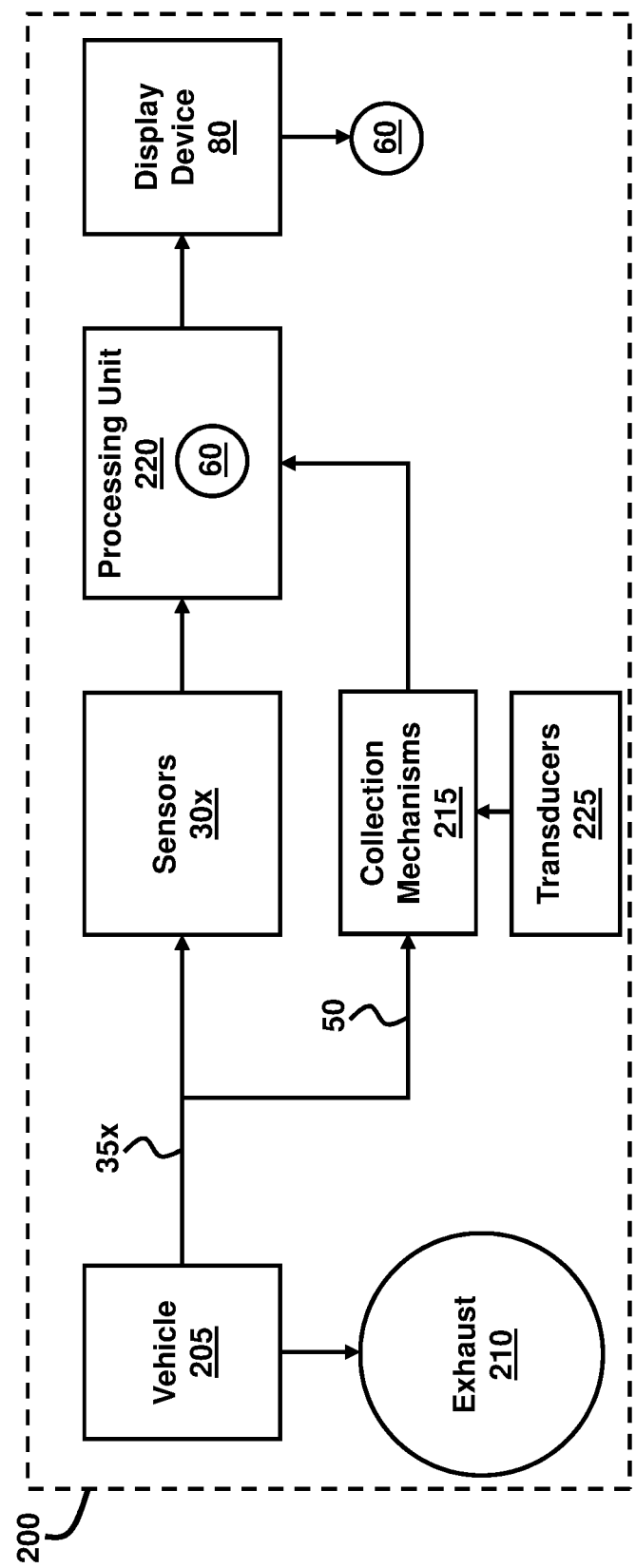
FIG. 10 is a block diagram illustrating the portable air quality measurement device of FIG. 9 with a plurality of transducers, according to an embodiment herein.

FIG. 10, with reference to FIGS. 1 through 9, illustrates that the portable air quality measurement device 200 comprises a plurality of transducers 225 operatively connected to the plurality of collection mechanisms 215. The plurality of transducers 225 are configured to control the operation of the plurality of collection mechanisms 215. In some examples, the plurality of transducers 225 may be either active or passive devices, and may be any of electromagnetic, electrochemical, electromechanical, and thermoelectric devices, or a combination thereof. The plurality of transducers 225 may be operatively connected and/or controlled by the processing unit 220 based on a pre-programmed set of instructions. In another example, the plurality of transducers 225 may be controlled based on user input. In an example, the plurality of transducers 225 may be fully disposed in the portable air quality measurement device 200. In another example, the plurality of transducers 225 may be partially disposed in the portable air quality measurement device 200. Moreover, the plurality of transducers 225 may be removably attached from the plurality of collection mechanisms 215 and/or the portable air quality measurement device 200 according to an example.

Figure 11:
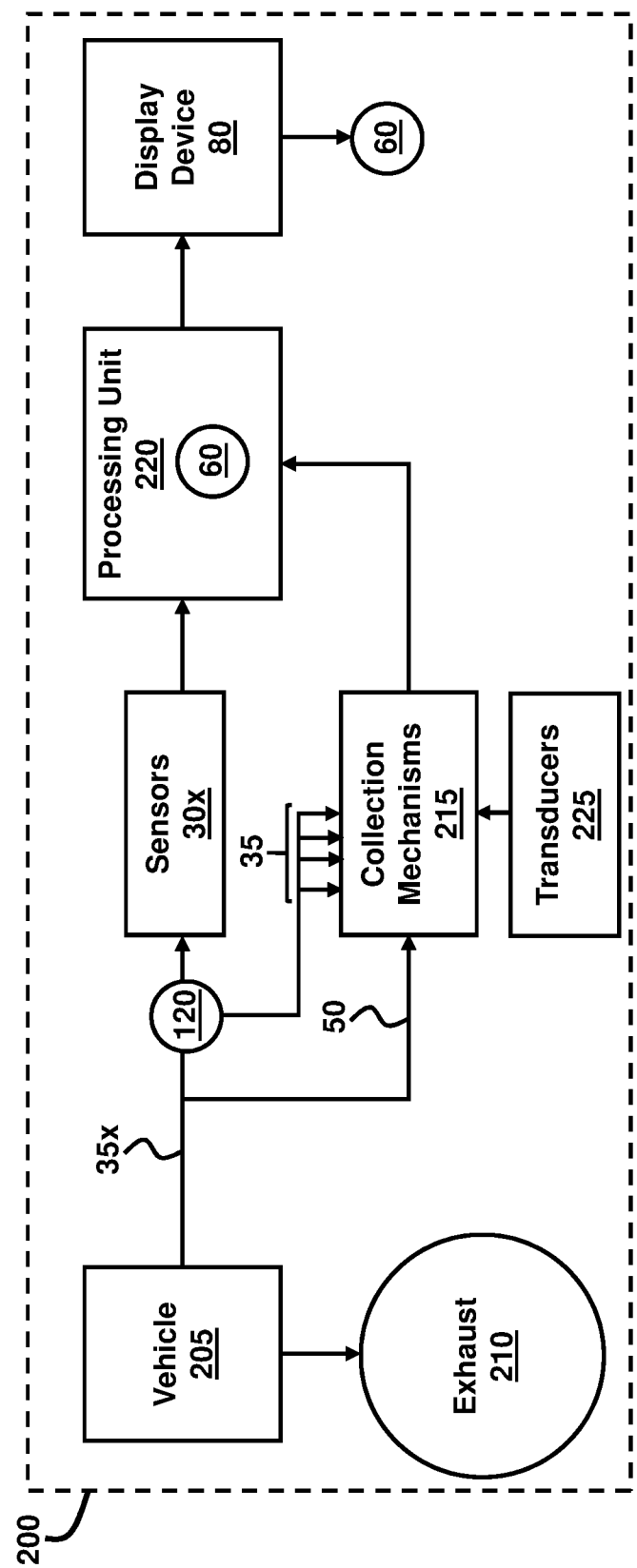
FIG. 11 is a block diagram illustrating the portable air quality measurement device of FIG. 9 with an air flow controller, according to an embodiment herein.

FIG. 11, with reference to FIGS. 1 through 10, illustrates that the portable air quality measurement device 200 comprises an air flow controller 120 to direct the plurality of air samples 35x to the plurality of collection mechanisms 215. In an example, each of the plurality of collection mechanisms 215 are configured to collect a separate air sample 35. In some examples, the air flow controller 120 may comprise an electrical device, magnetic device, electro-mechanical device, mechanical device, pneumatic device, or a combination thereof. The air flow controller 120 may control the mass flow rate of the plurality of air samples 35x in the portable air quality measurement device 200, in an example. In another example, the air flow controller 120 may comprise a fan to direct the plurality of air samples 35x to the plurality of collection mechanisms 215 and/or change the mass flow rate of the plurality of air samples 35x in the portable air quality measurement device 200 based on user input or a predetermined threshold for the mass flow rate of the plurality of air samples 35x. The air flow controller 120 may be positioned in the portable air quality measurement device 200 or may be outside of the portable air quality measurement device 200, or may be partially in/out of the portable air quality measurement device 200 according to some examples.

Figure 12:
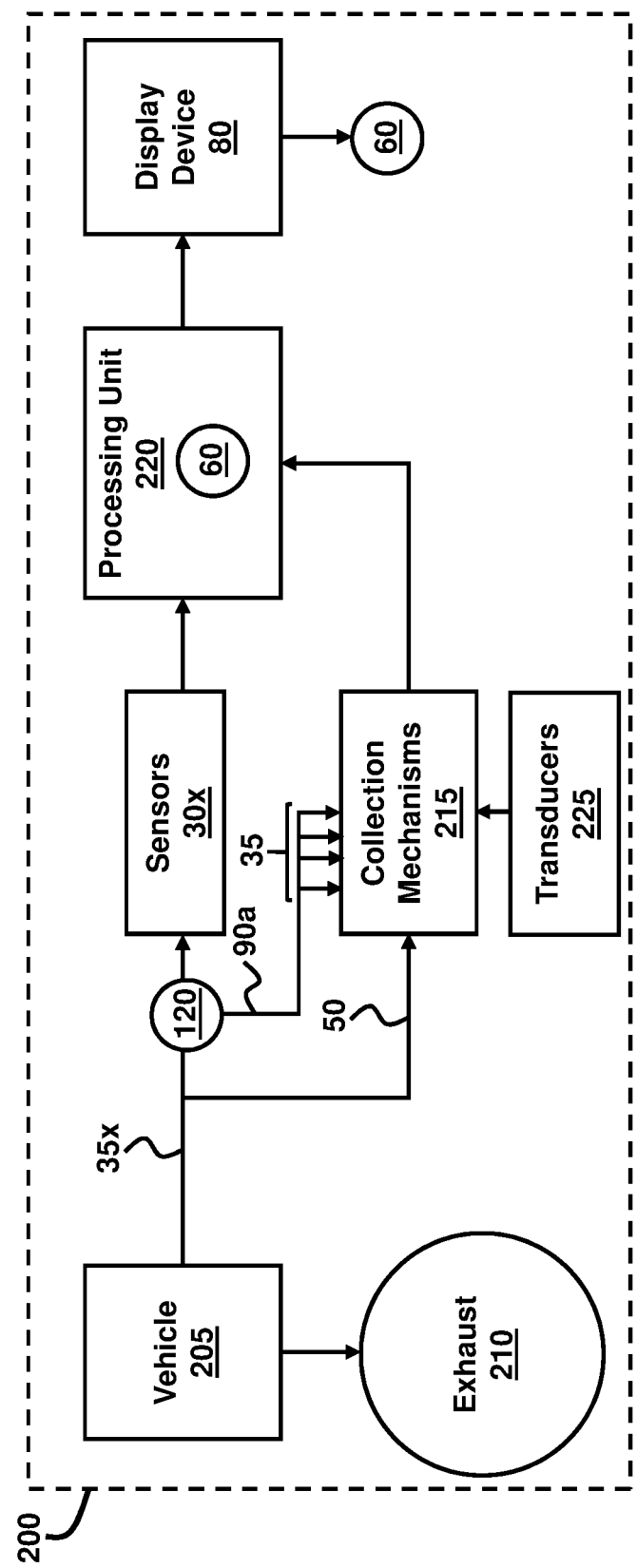
FIG. 12 is a block diagram illustrating the portable air quality measurement device of FIG. 11 with the air flow controller directing a flow of air, according to an embodiment herein.

FIG. 12, with reference to FIGS. 1 through 11, illustrates that, in an example, the air flow controller 120 directs a flow of air 90a of the plurality of air samples 35x of at least 10 LPM (liters per minute). In an example, the flow of air 90a may be the mass flow rate of the plurality of air samples 35x, which are directed towards the plurality of collection mechanisms 215. The air flow controller 120 may be controlled and/or programmed to alter the mass flow rate of the plurality of air samples 35x (e.g., the flow of air 90a). In an example, the operations of the air flow controller 120 may be controlled by the processing unit 220. In another example, the operation of the air flow controller 120 may be controlled based on preprogrammed instructions and settings associated with the air flow controller 120. Alternatively, the air flow controller 120 may be controlled by a user.

Figure 13:
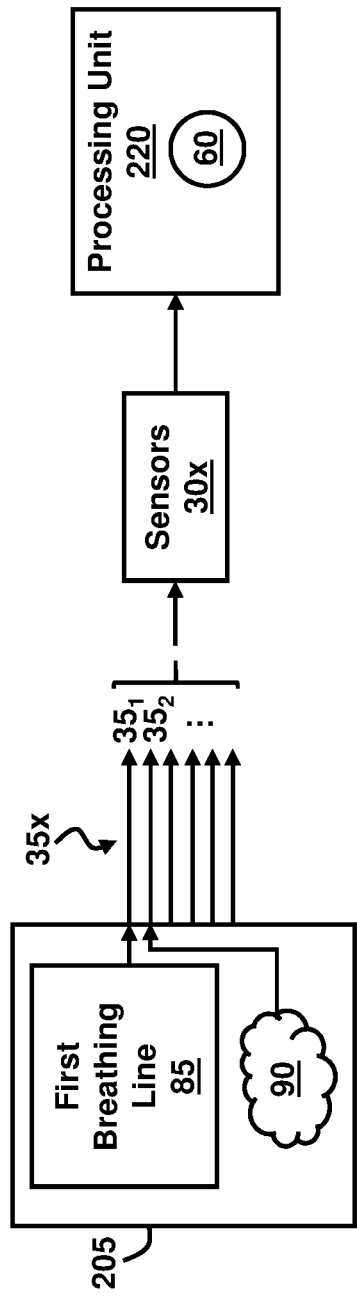
FIG. 13 is a block diagram illustrating the processing unit of the portable air quality measurement device of FIG. 9 performing real-time chemical analysis of air samples, according to an embodiment herein.

FIG. 13, with reference to FIGS. 1 through 12, illustrates that the plurality of air samples 35x comprises a first air sample $35_1$ from a first oxygen generation system breathing line 85 of the vehicle 205 and a second air sample $35_2$ comprising ambient air 90 from inside the vehicle 205. The processing unit 220 simultaneously performs the real-time chemical analysis 60 of both the first air sample $35_1$ and the second air sample $35_2$. The first air sample $35_1$ and the second air sample $35_2$ may be analyzed together, in an example. According to an example, the first air sample $35_1$ and the second air sample $35_2$ are distinct from one another and may comprise separate chemicals 50. Accordingly, the chemical analysis 60 may yield different results for the first air sample $35_1$ and the second air sample $35_2$, respectively. The first oxygen generation system breathing line 85 may comprise tubing, coils, pipes, or any other type of conduit capable of carrying and transmitting the first air sample $35_1$ to a driver's/pilot's air/breathing mask in the vehicle 205. In an example, the ambient air 90 may be collected from the driver compartment or cockpit of the vehicle 205.

Figure 14:
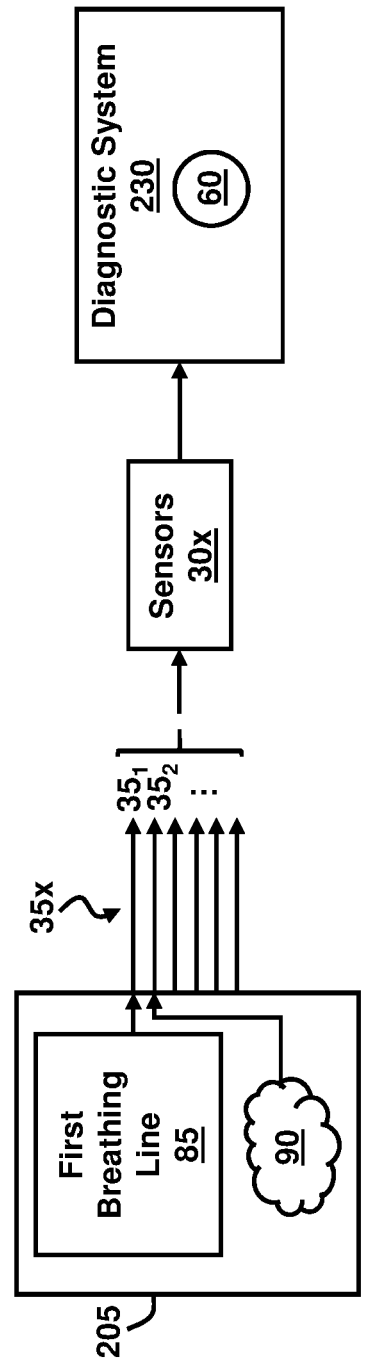
FIG. 14 is a block diagram illustrating the portable air quality measurement device of FIG. 9 with a diagnostic system performing real-time chemical analysis of air samples, according to an embodiment herein.

In some examples, as shown in FIG. 14, with reference to FIGS. 1 through 13, the real-time chemical analysis 60 may be performed by a diagnostic system 230. The diagnostic system 230 may be a standalone system remotely located, yet communicatively coupled to the portable air quality measurement device 200, or the diagnostic system 230 may be configured as part of the portable air quality measurement device 200.

Figure 15:
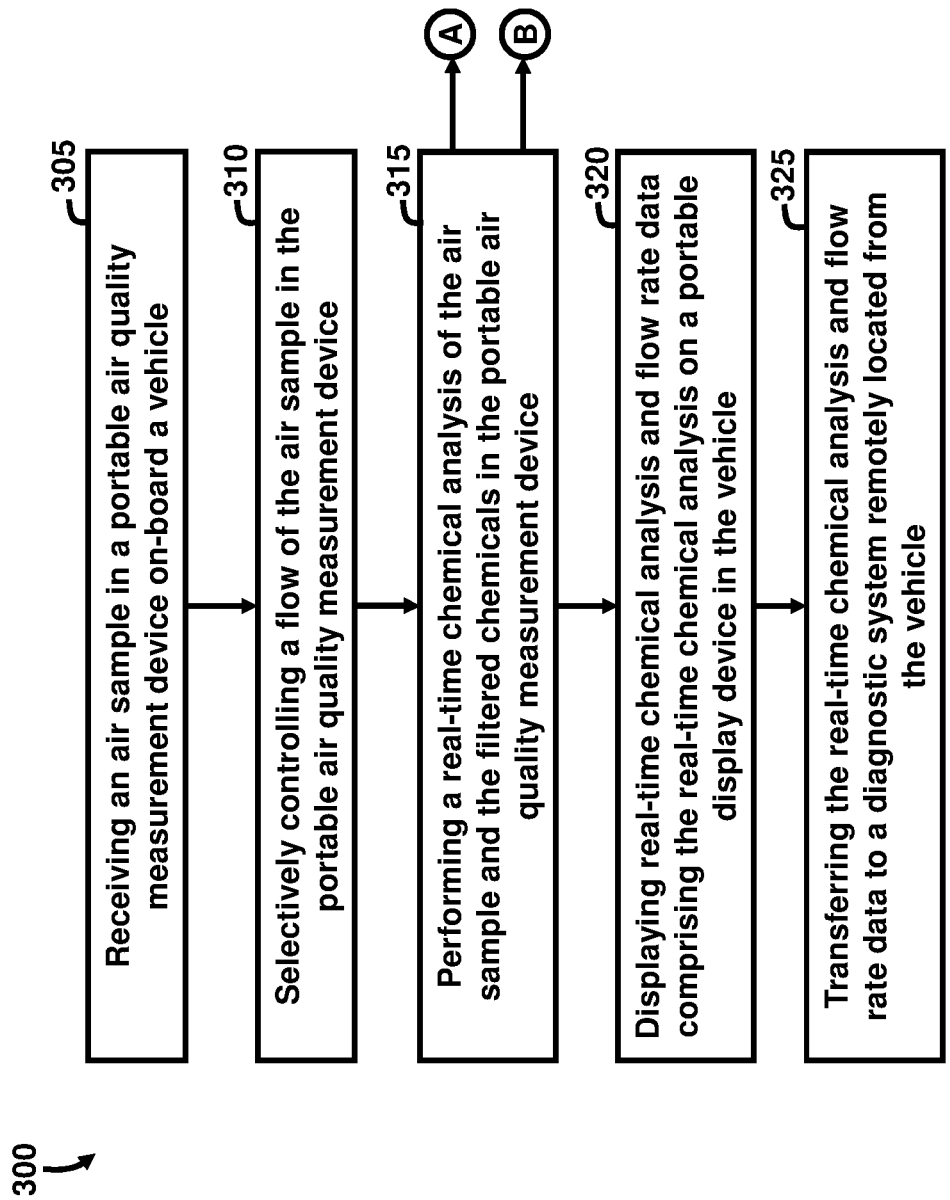
FIG. 15 is a flow diagram illustrating a method of measuring air quality, according to an embodiment herein.

FIG. 15, with reference to FIGS. 1 through 14, is a flow diagram illustrating a method 300 of measuring air quality. The method 300 comprises receiving (305) an air sample 35 in a portable air quality measurement device 200 on-board a vehicle 205, or an aircraft air quality testing system 10. As described above, the vehicle 205 may be an aircraft 20 in an example, and the portable air quality measurement device 200 may be placed on-board the vehicle 205; e.g., in the cockpit of an aircraft 20 to collect the air sample 35 from within the vehicle 205. The air sample 35 may be received by the portable air quality measurement device 200 using any of a pump 115, an air flow controller 120, and a mass flow meter 125 as well as collection media 45 or a plurality of collection mechanisms 215, among other components to assist in collecting the air sample 35 for input into the portable air quality measurement device 200. According to an example, the air sample 35 is provided during a plurality of oxygen generation system cycles and engine thrust settings 40 of the vehicle 205.

The method 300 further comprises selectively controlling (310) a flow (e.g., the mass flow rate of air 90a) of the air sample 35 in the portable air quality measurement device 200 or aircraft air quality testing system 10. The selective controlling (310) of the air sample 35 may occur using any of the pump 115, air flow controller 120, mass flow meter 125, first computer 65, second computer 100, processor 70, processing unit 220, diagnostic system 230, and a user, or a combination thereof. The air sample 35 may be further controlled by intaking a predetermined volume of air 90a based on a predetermined setting/threshold.

The method 300 further comprises performing (315) a real-time chemical analysis 60 of the air sample 35 and filtered chemicals 50 in the portable air quality measurement device 200 or aircraft air quality testing system 10. The filtering may occur by use of the removable collection media 45 or the plurality of collection mechanisms 215, which may comprise any suitable type of collection media such as filter material, thermal desorption tubes, and canisters, among other types of collection media or collection mechanisms. In some examples, the real-time chemical analysis 60 may be performed by any of the plurality of analyzers 55, processing unit 220, and diagnostic system 230. The real-time aspect of the chemical analysis 60 permits immediate results of the chemical analysis 60 of the air sample 35 thereby allowing a user to quickly determine the presence of any contaminants in the vehicle 205 or aircraft 20 and compare the concentrations to established exposure limits. According to some examples, the real-time chemical analysis 60 comprises an analysis of levels of carbon monoxide, carbon dioxide, nitrogen oxide, nitrogen dioxide, sulfur dioxide, oxygen, volatile organic compounds, ozone, ultrafine particles, relative humidity, air pressure, temperature, and mass flow rate of the air sample 35.

The method 300 further comprises displaying (320) real-time chemical analysis and flow rate data 60a comprising the real-time chemical analysis 60 on a portable display device 80 in the vehicle 205 or aircraft 20. Similarly, the real-time aspect of the chemical analysis and flow rate data 60a permits immediate results of the chemical analysis 60 of the air sample 35 to be displayed on the display device 80 thereby allowing a user to quickly determine the presence of any contaminants or irregularities in the vehicle 205 or aircraft 20, and particularly, in the first oxygen generation system breathing line 85 and/or the second oxygen generation system breathing line 95, and without having to transmit the chemical analysis and flow rate data 60a to a remote location for testing and analysis. The display device 80 may be portable and detachably connected to the portable air quality measurement device 200 or the portable housing unit 15 aircraft air quality testing system 10.

The method 300 further comprises transferring (325) the real-time chemical analysis and flow rate data 60a to a diagnostic system 230 remotely located from the vehicle 205. In this regard, additional and/or enhanced analysis of the real-time chemical analysis and flow rate data 60a may be performed by the diagnostic system 230, which may be located in a laboratory setting, in an example. The transferring (325) of the real-time chemical analysis and flow rate data 60a from the portable air quality measurement device 200 to the diagnostic system 230 may occur through wireless transfer, in an example.

FIG. 16, with reference to FIGS. 1 through 15, illustrates that the method 300 comprises performing (330) an off-line chemical analysis 105 of the filtered chemicals 50 and air sample 35 in the diagnostic system 230. The off-line chemical analysis 105 may include analysis such as spectroscopy, mass spectrometry, electrochemistry, calorimetry, chromatography, and microscopy, among other analysis techniques of the plurality of air samples 35x.

In an example, the chemicals 50 are filtered from the air sample 35 in a plurality of removable collection media 45 of the portable air quality measurement device 200. FIG. 17, with reference to FIGS. 1 through 16, illustrates that the method 300 further comprises sequencing (335) collection onto the removable collection media 45 to create a time stamp of the filtered chemicals 50. This permits the real-time chemical analysis 60 to include historic data trends associated with the air sample 35. For example, such information may be useful to determine whether the presence of contaminants in the breathable air (e.g., air in the first oxygen generation system breathing line 85, etc.) in the vehicle 205 changes over the course of a plurality of oxygen generation system cycles and engine thrust settings 40 of the vehicle 205. More particularly, in an example, this may demonstrate that the amount of chemical contaminants in the breathable air in the vehicle 205 increases over time thereby posing an enhanced health risk to the driver/pilot of the vehicle 205.

The embodiments herein may be used to characterize breathing air quality during engine ground run tests for any aircraft 20 to include all of the military fighters that employ the OBOGS, other aircraft employing liquid oxygen, and cargo aircraft. According to some examples, the aircraft air quality testing system 10 or portable air quality measurement device 200 may be used during routine maintenance to predict faults, as well as in response to unexplained physiological events of the pilot(s). In this regard, the aircraft air quality testing system 10 or portable air quality measurement device 200 revolutionizes the process for physiological event response and prevention due to the self-contained package of sampling techniques afforded by the compact size and portability of the aircraft air quality testing system 10 or portable air quality measurement device 200. Modular techniques, including the sampling unit 30 or plurality of sensors 30x and variable gas collection media 45 or plurality of collection mechanisms 215 allows for simultaneous OBOGS and aircraft cabin ambient breathing air sampling in a real-time scenario. This combination of the sampling unit 30, plurality of sensors 30x, collection media 45, and/or plurality of collection mechanisms 215 may be fastened directly into the first oxygen generation system breathing line 85 or the second oxygen generation system breathing line 95 of the aircraft 20 or vehicle 205 to provide real-time chemical analysis and flow rate data 60 to be transmitted directly to the first computer 65 and display device 80, which may be in the form of a tablet computer 65a mounted on the portable housing unit 15, while simultaneously collecting a plurality of air samples 35x for off-line chemical and particle analysis (e.g., off-line analysis 105).

In one embodiment, the device 200 connects into a manifold and has nine sensors. Another aspect of the embodiments herein is that the oxygen sensor has a range of 21%-96%, allowing accurate measurements of the very high oxygen levels the OBOGS system creates, from the perspective the pilots' respiratory system would see.

Accordingly, the embodiments herein are configured to characterize chemical contaminants during engine ground runs for advanced aircraft 20 to enable rapid characterization of oxygen concentrations and diagnosis of chemical contamination in breathing air. In use, the aircraft air quality testing system 10 or portable air quality measurement device 200 may rest on the lap of an operator while sitting in the cockpit of an aircraft 20. One flow path for collecting a plurality of air samples 35x from the ambient air 90 in the cockpit may be connected to an OBOGS regulator and the other flow path sitting in the ambient cabin. The instrumentation of the aircraft air quality testing system 10 or portable air quality measurement device 200 are set to collect the plurality of air samples 35x once the aircraft engine is started. The data is collected while the engine systematically goes through various oxygen generation system cycles and engine thrust settings 40 or operational activities and the collection media 45 or plurality of collection mechanisms 215 may be selectively replaced/substituted accordingly using a valve sequencing system. Once the engine run is completed, the collection media 45 or plurality of collection mechanisms 215 for off-line chemical analysis 105 is gathered and the next run collection media 45 or plurality of collection mechanisms 215 may be inserted into the aircraft air quality testing system 10 or portable air quality measurement device 200 while the available data (e.g., real-time chemical analysis and flow rate data 60a) may be transmitted to the first computer 65 for output on the display device 80.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Those skilled in the art will recognize that the embodiments herein can be practiced with modification within the spirit and scope of the appended claims.

What is claimed is:

1. An aircraft air quality testing system consisting of:
   a portable housing unit to be removably placed within an aircraft;
   an air testing unit secured inside the portable housing unit, the air testing unit comprising:
   a sampling unit to receive an air sample directly from both a cabin ambient air and an air supply for a pilot's mask during a plurality of oxygen generation system cycles and engine thrust settings of the aircraft;
   a removable collection media to receive the air sample from the sampling unit; and
   a plurality of analyzers to perform a real-time chemical analysis of the air sample;
   a first computer operatively connected to the portable housing unit, the first computer comprising:
   a processor to receive the real-time chemical analysis and flow rate and generate real-time chemical analysis and flow rate data;
   a memory device to store the real-time chemical analysis and flow rate data; and
   a display device operatively connected to the portable housing unit, wherein the display device is to output the real-time chemical and flow rate analysis data.

2. The system of claim 1, wherein the air testing unit is directly connected to a first oxygen generation system breathing line of the aircraft.

3. The system of claim 1, wherein the air testing unit is to collect ambient air from the aircraft or from a second oxygen generation system breathing line of the aircraft.

4. The system of claim 1, wherein the memory device comprises a removable memory device to connect to a second computer to perform an off-line analysis based on the real-time chemical analysis and flow rate data.

5. The system of claim 1, wherein the first computer comprises a tablet computer that is positioned on an outer surface of the portable housing unit.

6. The system of claim 1, wherein the plurality of analyzers are fully disposed in the portable housing unit.

7. The system of claim 1, comprising:
   a pump to pull a controlled volume of air over the collection media;
   an air flow controller to direct the air sample in the air testing unit; and
   a mass flow meter to monitor the flow of the air sample in the air testing unit.

8. The system of claim 1, comprising a valve to control a flow of air in the air testing unit.

9. The system of claim 1, comprising a power supply operatively connected to the air testing unit and the first computer.

10. A portable air quality measurement device consisting of: a plurality of sensors to receive a plurality of air samples directly from an air supply for a pilot's mask from within a vehicle that generates engine exhaust; a plurality of collection mechanisms to filter chemicals from the plurality of air samples; a processing unit to perform a real-time chemical analysis of the plurality of air samples; and a display device operatively connected to the processing unit to display the real-time chemical analysis.

11. The device of claim 10, comprising a plurality of transducers operatively connected to the plurality of collection mechanisms, wherein the plurality of transducers controls the operation of the plurality of collection mechanisms.

12. The device of claim 10, comprising an air flow controller to direct the plurality of air samples to the plurality of collection mechanisms, wherein each of the plurality of collection mechanisms are configured to collect a separate air sample.

13. The device of claim 12, wherein the air flow controller directs a flow of air of the plurality of air samples of at least 10 LPM (liters per minute).

14. The device of claim 10, wherein the plurality of air samples comprises a first air sample from a first oxygen generation system breathing line of the vehicle and a second air sample comprising ambient air from inside the vehicle, and wherein the processing unit simultaneously performs the real-time chemical analysis of both the first air sample and the second air sample.

15. The device of claim 10, wherein the plurality of sensors senses oxygen concentration levels in the range of approximately 21-96%.

16. A method of measuring air quality, the method consisting of: receiving an air sample directly from both a cabin ambient air and an air supply for a pilot's mask in a portable air quality measurement device on-board a vehicle; selectively controlling a flow of the air sample in the portable air quality measurement device; performing a real-time chemical analysis of the air sample and filtered chemicals in the portable air quality measurement device; displaying real-time chemical analysis and flow rate data comprising the real-time chemical analysis on a portable display device in the vehicle; and transferring the real-time chemical analysis and flow rate data to a diagnostic system remotely located from the vehicle.

17. The method of claim 16, further comprising, receiving the air sample during a plurality of oxygen generation system cycles and engine thrust settings of the vehicle.

18. The method of claim 16, comprising performing an off-line chemical analysis of the air sample and filtered chemicals in the diagnostic system.

19. The method of claim 16, wherein the chemicals are filtered from the air sample in a plurality of removable collection media of the portable air quality measurement device, and wherein the method further comprises sequencing collection onto the removable collection media to create a time stamp of the filtered chemicals.

20. The method of claim 16, wherein the real-time chemical analysis comprises an analysis of levels of carbon monoxide, carbon dioxide, nitrogen oxide, nitrogen dioxide, sulfur dioxide, oxygen, volatile organic compounds, ozone, ultrafine particles, relative humidity, air pressure, temperature, and mass flow rate of the air sample.

* * * * *